United States Patent [19]
Aikins

[11] Patent Number: 4,491,132
[45] Date of Patent: Jan. 1, 1985

[54] SHEATH AND RETRACTABLE SURGICAL TOOL COMBINATION

[75] Inventor: Jerry L. Aikins, Warsaw, Ind.

[73] Assignee: Zimmer, Inc., Warsaw, Ind.

[21] Appl. No.: 405,843

[22] Filed: Aug. 6, 1982

[51] Int. Cl.³ .............................................. A61B 17/32
[52] U.S. Cl. ........................................ 128/305; 30/162
[58] Field of Search ............... 128/305, 304, 751, 757, 128/303.15, 303 R, 3; 30/162, 295

[56] References Cited

U.S. PATENT DOCUMENTS

| | | | |
|---|---|---|---|
| Re. 30,733 | 9/1981 | Quenot | 30/162 |
| D. 263,020 | 2/1982 | Rau | D8/99 |
| 651,395 | 6/1900 | Stapp | 128/304 |
| 1,493,240 | 5/1924 | Bohn. | |
| 2,496,111 | 1/1950 | Turkel | 128/2 |
| 2,885,780 | 5/1959 | Campbell | 30/162 X |
| 3,007,471 | 11/1961 | McClure, Jr. | 128/2 |
| 3,468,312 | 9/1969 | Kuntscher | 128/317 |
| 3,472,229 | 10/1969 | Kuntscher | 128/317 |
| 3,762,416 | 10/1973 | Moss et al. | 128/305 |
| 3,835,859 | 9/1974 | Roberts et al. | 128/305 |
| 4,010,737 | 3/1977 | Vilaghy et al. | 128/2 B |
| 4,063,555 | 12/1977 | Ulinder | 128/214 R |
| 4,067,340 | 1/1978 | LeNoir | 128/305 |
| 4,338,952 | 7/1982 | Augros | 128/757 |
| 4,414,974 | 11/1983 | Dotson et al. | 30/162 X |
| 4,444,184 | 4/1984 | Oretorp | 128/305 |

FOREIGN PATENT DOCUMENTS

| | | | |
|---|---|---|---|
| 2506600 | 12/1982 | France | 128/305 |

Primary Examiner—Michael H. Thaler
Attorney, Agent, or Firm—Margaret L. Geringer

[57] ABSTRACT

A surgical instrument comprising a scalpel handle with a separate protective sheath for use in closed surgical procedures, such as arthroscopy. The protective sheath provides for atraumatic insertion of a scalpel blade into the body and to the actual operative site, minimizing the chance of accidental cutting of surrounding tissue. The handle portion is insertable into the tubular sheath from the distal tubular opening of the sheath. The sheath and handle combination may be engaged relative to each other in a plurality of functional positions.

14 Claims, 22 Drawing Figures

SHEATH AND RETRACTABLE SURGICAL TOOL COMBINATION

BACKGROUND OF THE INVENTION

The present invention generally relates to surgical instruments, and more particularly to surgical instruments used in arthroscopic surgery.

Arthroscopic surgery is typically performed through very small incisions to enable a surgeon to examine a joint and perform certain surgical procedures on a joint through the small incisions. Arthroscopic surgery is typically performed through three small one-fourth inch incisions while the patient is under general anesthesia. A fiber optic telescope or arthroscope, smaller than the size of a pencil, is inserted into one of the incisions for allowing the surgeon to thoroughly examine all parts of the joint. A small television camera may be attached to the arthroscope and the magnified image of the inside of the joint is displayed on a television screen. Small delicate instruments are inserted through one of the other small incisions, and the damaged portion of the joint may be repaired or corrected. The small incisions avoid the large scars of a conventional open surgical operation and shorten the patient's recovery time while reducing postoperative pain.

One such small instrument often used in arthroscopy is a cutting instrument. As is known in the art, the use of a protective sheath provides a means of atraumatic insertion of the cutting instrument into the body to the actual cutting site. This minimizes the chance of accidental cutting of surrounding tissue. The cutting blade is attached to a blade handle, and is maintained retracted within the sheath prior to use. After positioning of the distal end of the sheath near the cutting site, the blade and blade handle may be moved forward within the sheath to expose the cutting edge or blade from the distal end of the sheath.

Figure 1:
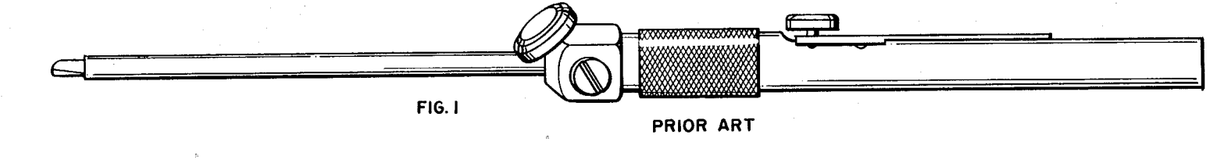
FIG. 1 is a pictorial view of a prior art blade/blade handle and sheath combination.
Figure 2:
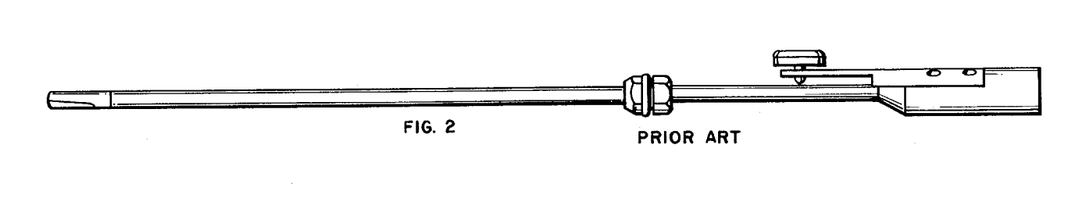
FIG. 2 is a pictorial view of the prior art blade/blade handle of FIG. 1.
Figure 3:
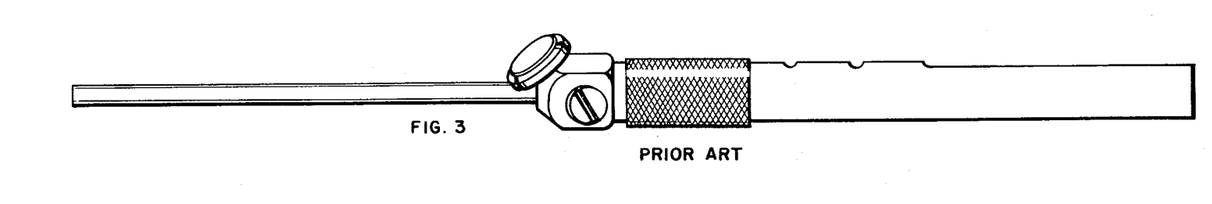
FIG. 3 is a pictorial view of the prior art sheath of FIG. 1.

An example of a prior art surgical knife/sheath combination is shown in FIGS. 1, 2, and 3 herein. This device provides two functional positions for the handle relative to the sheath. In one position, the blade attached to the handle is exposed for cutting and in the other position, it is withdrawn completely within the protective sheath for insertion or withdrawl. The blade handle with the blade secured thereto is introduced into the sheath through its proximal end until the handle is locked into either of the two positions. This insertion of the blade from the proximal end through the length of the sheath undesirably exposes the blade to dulling by contacting the inner walls of the sheath throughout the length of the sheath as the blade is advanced toward the distal end of the sheath. Also, when a new blade is required, the blade handle must be completely removed from the sheath, the blade changed and the blade handle reinserted through the sheath, again risking dulling of the new blade.

In this prior art device, the mechanism for selectively positioning or locking the blade handle in position with respect to the sheath is a mechanism which is external to the sheath. The blade handle includes an enlarged proximal portion with one end of a cantilever spring mechanism attached thereto and extending toward the distal end of the blade handle. A knob (including a protruding pin portion) is attached to the opposite end of the cantilever spring mechanism. A slot is provided on the proximal end of the sheath which enables the cantilever spring to remain external to the sheath as the blade handle is inserted. The protruding pin on the knob may then be positioned in either one of two corresponding holes provided in the sheath. The proximally located hole corresponds to the retracted blade position and the distal hole corresponds to the exposed blade position. The blade handle can not be extended any further than this exposed position. This arrangement disadvantageously requires both hands of the surgeon to change the blade handle from one position to the other: one hand to hold the sheath and the other to pull up on the knob and slide the blade handle to the appropriate position.

OBJECTS OF THE INVENTION

A principle object of the present invention is to overcome the disadvantages of the prior art.

A main object of the invention is to provide a scalpel blade handle with a protective sheath in which the blade/blade handle is insertable through the distal end of the sheath so that the blade is not advanced through the sheath so as not to risk blade dulling which can occur when the blade and blade handle are inserted through the proximal end of the sheath.

Another object of the invention is to provide a scalpel blade handle with a protective sheath which provides a plurality of functional positions between the blade handle and the sheath including a fully retracted blade position and an exposed blade position for cutting.

A further object of the invention is to provide a scalpel blade handle with a protective sheath in which the surgeon can manipulate the blade from a fully retracted and protective position to an operable exposed position and vice versa with one hand, leaving the surgeon's other hand free.

A still further object of the invention is to provide a scalpel blade handle with a protective sheath in which the blade can be replaced without having to completely remove the blade handle from the sheath.

An additional object of the invention is to provide a scalpel blade handle with a protective sheath which is small in size and lightweight, enhancing the surgeon's sense of "feel" with the instrument.

A still further object of the invention is to provide a scalpel blade handle with a protective sheath which is simple to manufacture and simple to assemble for use.

An additional object of the invention is to provide a scalpel blade handle with a protective sheath which enables the surgeon to hold and directly manipulate the blade handle giving the surgeon more control and better "feel" of the cutting action. This is as opposed to the surgeon holding and manipulating the sheath (as in the previously discussed prior art device), and hence indirectly manipulating the blade handle.

SUMMARY OF THE INVENTION

The present invention accomplishes all of the above objects of invention. The present invention will be described with reference to a scalpel instrument although it is understood that this invention could be applied to other surgical instruments where a protective sheath is advantageous or required. The present surgical tool utilizes a scalpel blade handle with a protective sheath which is particularly advantageous for use in arthroscopic procedures. The protective sheath provides a means of atraumatic insertion of a scalpel blade into the body and to the actual operative site, minimizing the chance of accidental cutting of surrounding tissue. The blade/blade handle and sheath may be made out of any suitable material. One such suitable material would be stainless steel.

The blade/blade handle portion is preferably insertable into the thin walled tubular sheath from the distal opening of the sheath. This prevents the blade from having to be advanced through the sheath which would risk dulling the blade from potential contact with the inner walls of the sheath as the blade/blade handle is advanced.

The present blade handle and sheath combination provides three functional positions. A suitable locking or engaging means is provided between the handle and the sheath in order to lock the handle in the desired position relative to the sheath. The following three functional positions are provided in a particularly advantageous embodiment of the invention: (1) the cutting blade is withdrawn completely within the sheath for insertion to and removal from the operative site; (2) the blade is partially exposed for use in tight quarters, as is often the case in endoscopic procedures; and (3) the blade is fully exposed for use where space is not constrained.

The blade also can be replaced without having to completely remove the blade handle from the sheath. The blade handle is just withdrawn slightly from the distal end of the sheath exposing a simple blade holding mechanism. The blade is replaced, and then the blade handle is repositioned back into the sheath in the desired functional position.

BRIEF DESCRIPTION OF THE DRAWINGS

These features and objects of the invention, as well as others, will become apparent to those skilled in the art by referring to the accompanying drawings in which:

FIG. 9 A is a pictorial view of the instrument of FIG. 4 in which manual pressure is being applied to the most proximal portion of the sheath in order to deflect the cantilever spring and disengage the position locking mechanism;

FIG. 9 B is a pictorial view of the instrument of FIG. 4 which illustrates an alternate manner of holding the instrument in order to apply manual pressure to the most proximal portion of the sheath in order to deflect the cantilever spring and disengage the position locking mechanism.

DETAILED DESCRIPTION OF THE INVENTION

FIGS. 4 through 21 illustrate a particularly advantageous embodiment of the surgical instrument of the present invention. The instrument includes a protective sheath 10 and a blade handle 40 which is insertable in the sheath 10.

Figure 7:
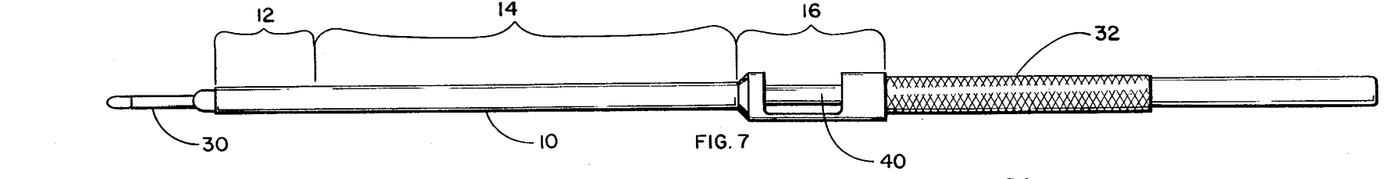
FIG. 7 is a side view of the instrument of FIG. 4 except the blade is in its fully exposed functional position.

As shown in FIG. 7, the sheath 10 includes a distal end 12, a proximal portion 16 and an intermediate portion 14 integrally disposed therebetween. The sheath 10 is a thin-walled elongated stepped tube. The intermediate and distal tube portions 14 and 12 preferably have a smaller diameter than the proximal portion 16. In arthroscopic procedures, it is essential to have a small diameter sheath for insertion into the body as the opening to the surgical site is typically small. It is preferred that the smaller distal and intermediate portions have a maximum outside diamter of 5 mm. The larger proximal portion 16 will remain outside the body and therefore, the larger diameter is acceptable.

Figure 13:
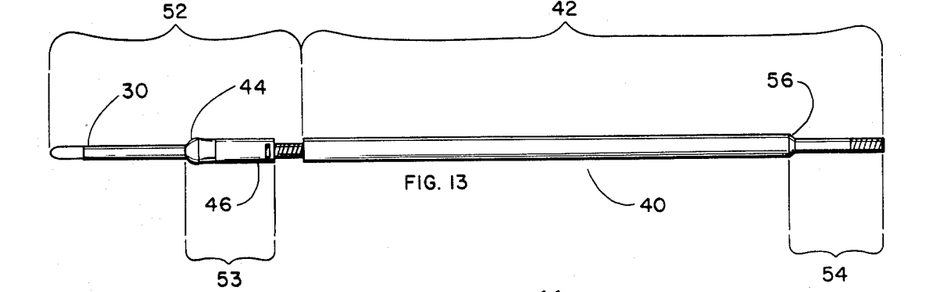
FIG. 13 is a side view of the blade and blade handle.
Figure 14:
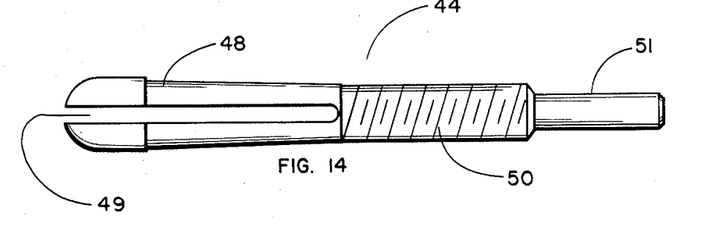
FIG. 14 is an enlarged side view of the blade holding chuck of FIG. 13.
Figure 15:
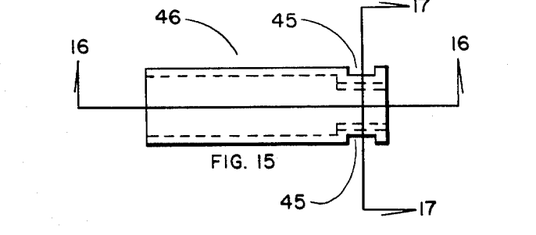
FIG. 15 is an enlarged side view of the collar of FIG. 13.
Figures 16, 17:
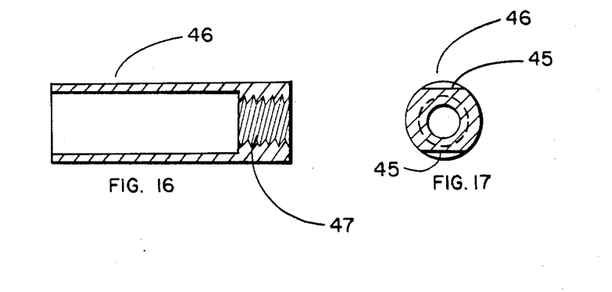
FIG. 16 is a cross-sectional view of the collar taken along lines 16—16 of FIG. 15.
FIG. 17 is a cross-sectional view of the collar taken along lines 17—17 of FIG. 15.

The blade handle 40 is illustrated in FIG. 13 and is comprised of a thin elongated main body portion 42 (shown in FIGS. 19 and 20) and a distal end portion 52. The distal end 52 provides the working end of the surgical tool. In the instrument embodiment shown, the distal end includes a separable scalpel blade 30 and a suitable blade holding means 53 (shown in FIGS. 13 to 17). The blade holding means is comprised of a chuck 44 and a collar 46. The chuck 44 includes a slotted, two jaw chuck 48 which forms blade slot 49, attached to one end of a thin threaded shaft 50. A thinner rod portion 51 extends from the opposite end of the threaded shaft 50. The two jaw portion 48 of the chuck 44 tapers outward as it progresses from its point of attachment to the threaded shaft 50 out toward the distal tip of the chuck 44. The collar 46 (see FIGS. 15 and 16) is a hollow sleeve which includes an internally threaded portion 47 at one end. The collar 46 fits over the thinner rod portion 51 and over the threaded rod portion 50 of the blade holding means 53. The threaded portion 47 of the collar engages the threaded shaft 50 of the chuck assembly 44. As the collar 46 is rotated further onto the threaded shaft 50, the unthreaded hollow sleeve portion of collar 46 tightens up onto the tapered jaw portion 48 causing the two jaws to move inward toward slot 49. After the collar 46 is attached to the threaded shaft 50, the thinner rod portion 51 is securely attached into a corresponding internal hole 43 (see FIG. 19) in the main body portion 42 to become part of the blade handle 40. Portion 51 may be press fit into hole 43.

Therefore, to insert a suitable scalpel blade 30 into the chuck 44, the collar 46 is loosened so that the slot 49 is able to receive the flat blade 30. Then the collar 46 is threadedly advanced over the tapered two jaw portion 48 tightening the two jaws 48 onto the blade 30. Flats or slots 45 may be provided on the collar 46 in order to facilitate the tightening of the collar 46 about the chuck 44 with a suitable wrench tool such as the tool 34 shown in FIG. 18. In order to remove the blade, the above procedure is simply reversed. It is understood that the blade holding means is not limited to the above-described style, but that any suitable blade securing means could be suitably utilized in conjunction with the main body portion 42 of the blade handle 40. The blade and blade handle may even be formed integrally as one piece if it is not necessary to have separable and replaceable blades.

The main body portion 42 of the blade handle 40 has a slender cylindrical shape having primarily a uniform diameter throughout its length, although the very proximal end 54 may step down to a smaller diameter.

The blade handle 40 and sheath 10 combination includes an engaging means which will be operative between the sheath 10 and the blade handle 40. The engaging means provides a plurality of functional positions for the blade handle 40 to be selectively positioned within the sheath 10.

Figure 10:
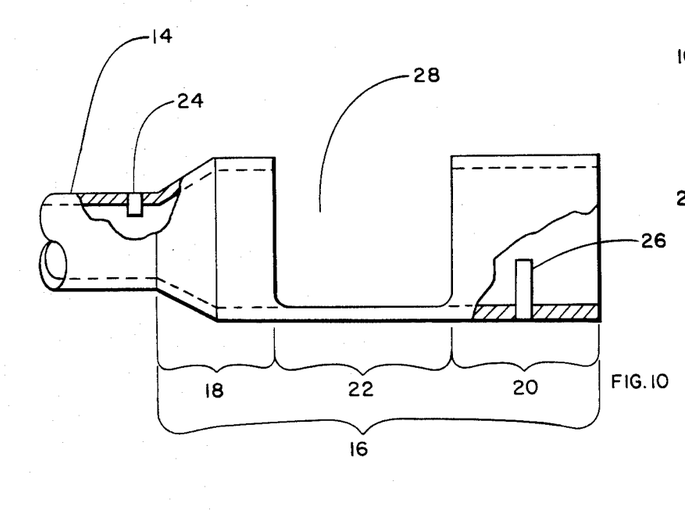
FIG. 10 is an enlarged side view of the proximal end of the sheath shown in partial cross-section.
Figure 11:
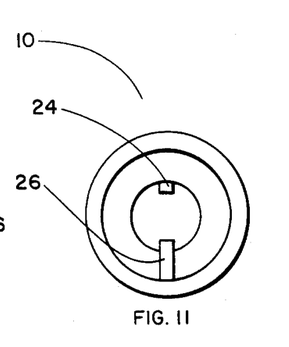
FIG. 11 is an enlarged end view of the sheath of FIG. 10 looking into the proximal opening of the sheath.
Figure 12:
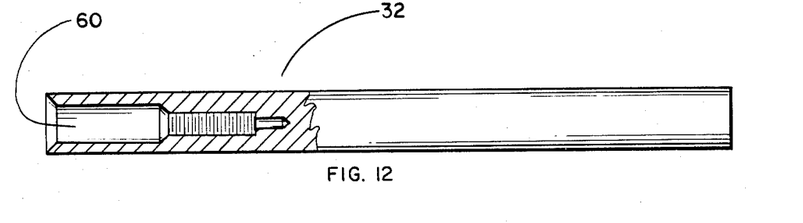
FIG. 12 is an enlarged side view of the handle extension shown in partial cross-section.

The proximal portion 16 of the sheath 10 forms part of the engaging means. A large window 28 is formed in the proximal portion 16 of the sheath 10 forming a thin resilient strip 22 which acts as a cantilever spring mechanism. The window divides the proximal portion, forming a first proximal portion 18 and a second proximal portion 20 connected together by the cantilever spring 22, as shown in FIG. 10. The first portion 18 is integrally connected to the intermediate sheath portion 14, and the second portion 20 forms the most proximal portion of the sheath 10.

In cooperation with the cantilever spring mechanism 22, the engaging means further includes a cooperative mechanism which is operative internally between the blade handle component 40 after it has been inserted into the sheath component 10. This mechanism is comprised of a protrusion means on one component and an indentation means on the other component which cooperatively engage with each other. An example of such a protrusion and indentation means is further described below.

Figure 4:
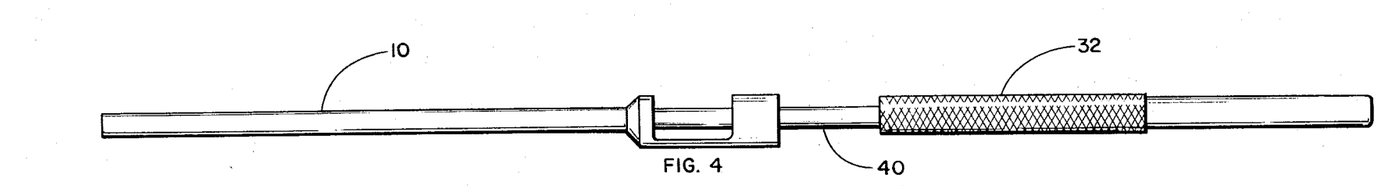
FIG. 4 is a side view of a particularly advantageous embodiment of the blade handle and sheath combination of the present invention illustrating the instrument with the blade completely withdrawn into the sheath.
Figure 20:
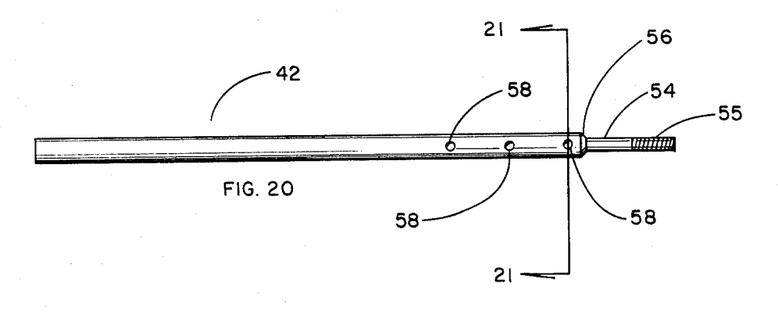
FIG. 20 is a bottom view of the main body portion of the blade handle of FIG. 13.
Figure 21:
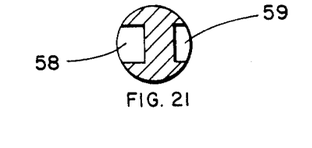
FIG. 21 is a cross-sectional view of the main body portion taken along lines 21—21 of FIG. 20.

FIG. 10 illustrates a protruding engagement pin 26 extending from the bottom inside surface of the second proximal portion 20 of the sheath 10. FIG. 20 illustrates a plurality of indentations or holes 58 on the bottom side of the main body portion 42 of the blade handle. The holes 58 are aligned so that as the pin 26 engages into one of the holes 58, this locks the handle 40 position relative to the sheath 10. The embodiment shown provides for three functional positions between the blade handle 40 and the sheath 10. (It is noted that the terms describing the orientation of certain features of the instrument, such as top and bottom, are defined in relation to the orientation of the instrument as illustrated in FIGS. 4–8, 9 and 10. It is understood that these terms are used for convenience in understanding the invention description, and that this orientation could be varied. For example, if the instrument was rotated 180°, the "top" would then become the "bottom." FIG. 9 B is an example of this "rotated" orientation. Other than in reference to this FIG. 9 B, the terms top and bottom are chosen to refer to the orientation such as is illustrated in FIG. 4.)

In order to ensure that the blade handle is oriented so as to align the holes 58 directly with the pin 26, another pin 24 protrudes from the inner diameter of the intermediate portion 14 of the sheath 10 (see FIG. 10). This protruding alignment pin 24 cooperates with an elongated slot 59 (shown in FIG. 19) located on the main body portion 42 of the blade handle 40. Upon initial insertion of the blade handle 40 into the sheath 10, the blade handle 40 is stopped by pin 24. Then handle 40 is rotated until slot 59 aligns with pin 24, and then insertion of the handle 40 continues. This aligning mechanism is positioned to ensure that the pin 26 will be in alignment with the holes 58. This alignment pin 24 also positively orients the direction of the blade with respect to the sheath. The aligning pin 24 also prevents rotation of the handle 40 with respect to the sheath 10 when the handle is only partially inserted into the sheath. (See FIG. 8.) In this position, blades 30 can be inserted or replaced while the handle 40 is prevented from rotating in the sheath 10.

Figure 9A:
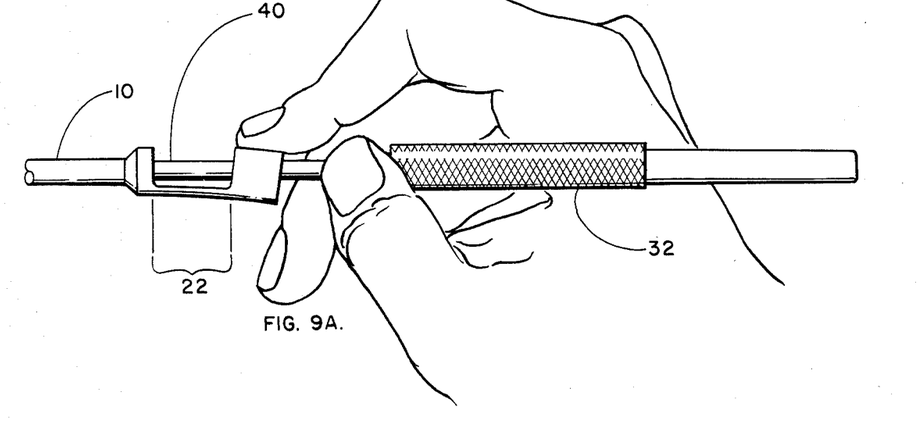

When the pin 26 is engaged with one of the holes 58, the position of the blade handle 40 is locked in relation to the sheath 10. In order to disengage this locked position or to change functional positions between the handle 40 and the sheath 10, simple manual finger pressure is exerted on the second proximal portion 20 of the sheath 10 on the side of the sheath 10 opposite the pin 26. (Refer to FIG. 9 A). This pressure deflects the cantilever spring 22 and lifts or disengages the locking pin 26 out of the hole 58 in the handle 40 which unlocks the sheath 10 from the handle 40 for changing blade position.

Figure 9B:
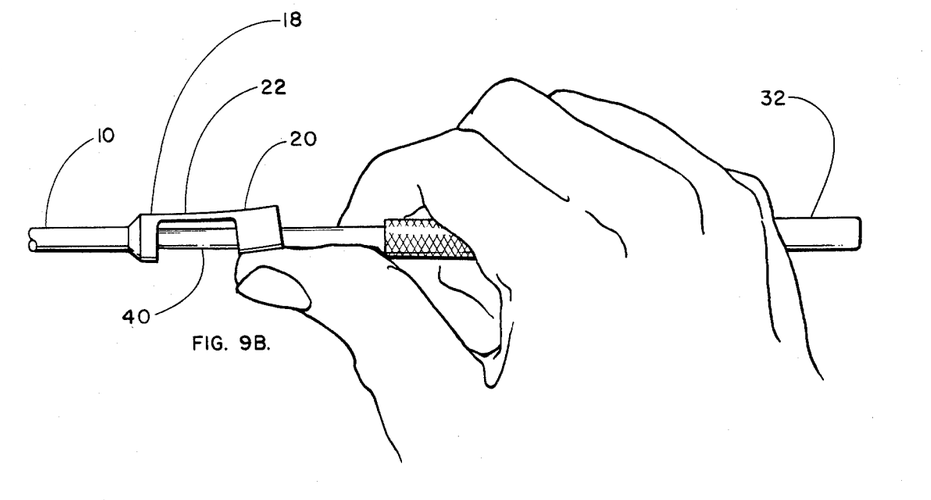

It is understood that the surgeon may hold the instrument in whatever manner he considers most desirable. FIG. 9 A illustrates the cantilever spring 22 being deflected downward by the index finger. FIG. 9 B illustrates the instrument being held with the cantilever spring 22 at a different orientation, and illustrates the spring 22 being deflected upward by the thumb.

The pin 26 could be located on the top inner wall of the second proximal portion 20 with the corresponding holes 58 aligned accordingly, if desirable. (Opposite to the location shown in FIG. 10.) Then to change blade positions, the finger pressure is still applied on the side of the second proximal sheath portion 20 opposite the pin 26.

Figure 18:
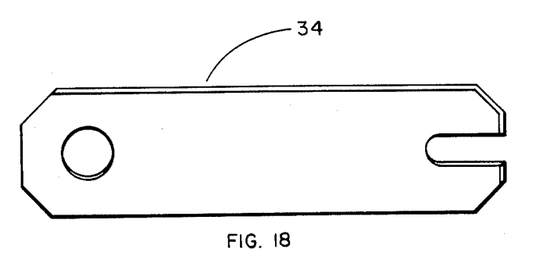
FIG. 18 is an enlarged pictorial view of a suitable wrench instrument for use with the blade holding chuck and collar mechanism of FIG. 13.
Figure 19:
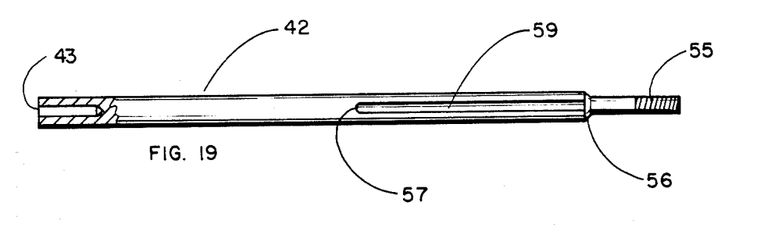
FIG. 19 is a top view of the main body portion of the blade handle of FIG. 13 shown in partial cross-section.

In using this sheath/blade handle combination, the user takes in hand the blade handle 40 which has not yet been inserted in the sheath 10. If a blade 30 is not already positioned in the blade handle 40, the collar 46 is loosened from the chuck 44. A suitable cutting blade 30 is inserted in the slot 49 with the cutting edge protruding from the chuck 44. The collar 46 is tightened over the tapered chuck 44 to lock the blade 30 in place. A wrench 34 (such as is shown in FIG. 18) may be used to ensure that the blade 30 is tightly secured.

The proximal end 54 of the blade handle 40 is inserted into the distal opening in the sheath 10. There is minimal clearance between the outer diameter of the blade handle 40 and the inner diameter of the sheath 10. As the handle 40 proceeds into the sheath 10, but before the threaded shaft 50 has been withdrawn into the sheath, the handle 40 is stopped by pin 24. The handle 40 is rotated until pin 24 aligns with slot 59 (refer to FIG. 8 for approximate positioning at this point). Insertion of the handle 40 continues. The thinner proximal portion 54 of the blade handle clears the second protruding pin 26 and then protrudes from the second proximal end 20 of the sheath 10. The handle 40 is stopped as pin 26 interferes with the larger diameter of the blade handle 40. A ramp 56 is provided so the pin slides easily up onto the larger diameter of the handle 40 deflecting the cantilever spring 22. The handle 40 is then pulled just a little further into the sheath causing pin 26 to lock into the most proximally located hole 58.

Figure 8:
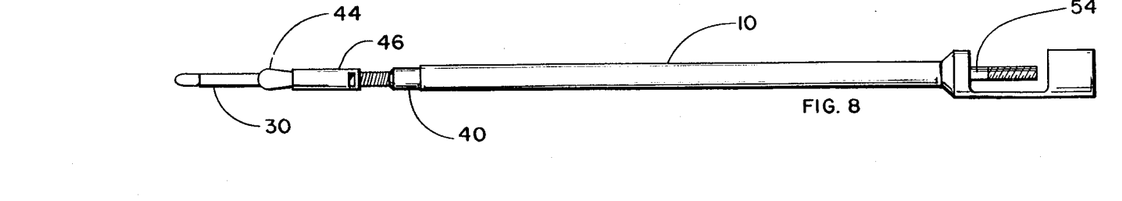
FIG. 8 is a side view of the instrument of FIG. 4 except the blade handle extension has been removed and the blade handle has been partially withdrawn from the distal end of the sheath exposing the blade holding chuck mechanism.

At this position, it is convenient to attach handle extension 32. (Refer to FIG. 7 for positioning at this point.) Although any convenient attachment means may be used, a convenient attachment means is to include a threaded portion 55 on the proximal end 54 of the blade handle 40 which is threaded into a corresponding hole 60 in the handle extension 32. This extension 32 enables the portion of the handle extending from the proximal end of the sheath to be a little larger in diameter for the user holding the handle. Since the blade handle 40 is designed to be inserted through the sheath 10 from the distal end of the sheath 10, in order to provide a larger diameter handle extension, it must be attachable after the blade handle 40 has been inserted through the sheath, since the larger diameter extension 32 would not fit through the smaller diameter of the distal and intermediate sheath portions 12 and 14. Also, as shown in FIG. 8, the larger diameter handle is not attached or has been removed in order to expose the distal end portion 52 (referenced in FIG. 13) to enable blades 30 to be inserted or replaced in this position, as previously discussed. Alternatively, blade handle 40 could be further elongated to provide an integral handle means which extends beyond the sheath (not illustrated), preferably which does not have a larger diameter, thus still enabling insertion of the blade handle 40 from the distal end of the sheath. In either case with the handle extension 32 or with an integral elongated handle, this enables the surgeon to directly manipulate the blade handle 40 instead of the sheath (such as is the case with the prior art device of FIGS. 1-3, in which the surgeon manipulates the sheath). Directly manipulating the handle (instead of the sheath) allows for better "feel" by the surgeon of the cutting action. With the separately attachable extension 32, though, this enables the extending handle portion to have a slightly larger diameter. The handle extension may be knurled for better grip, or it may even have an irregular (not a straight shaft) shape conforming to a comfortable hand grip since the extension 32 is attached after the handle 40 has been inserted through the sheath 10.

Figure 6:
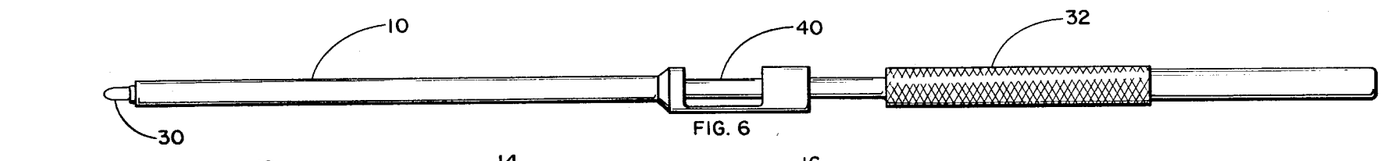
FIG. 6 is a side view of the instrument of FIG. 4 except the blade is in its partially exposed functional position.

FIG. 7 illustrates the blade in a fully exposed position. In this position, the pin 26 is engaged with the most proximal hole 58. To change positions to the partially exposed blade position, the cantilever spring 22 is deflected to disengage pin 26 from the hole. The sheath 10 is pushed forward by the thumb or finger until pin 26 engages in the next hole (in this case, the middle hole). Refer to FIG. 6 which illustrates this position.

Figure 5:
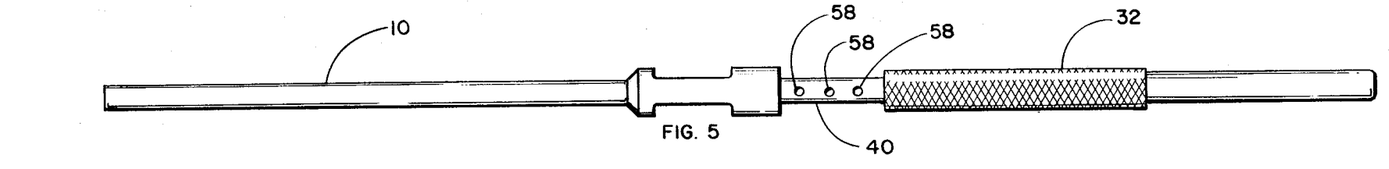
FIG. 5 is a bottom view of the instrument illustrated in FIG. 4.

To change blade position to the completely withdrawn blade position, the spring 22 is again deflected and the sheath moved forward until the pin 26 engages with the next hole 58 (in this case the most distally located hole 58). FIGS. 4 and 5 illustrate the fully withdrawn position. In this position the blade is completely withdrawn into the sheath.

If the user attempts to deflect the spring 22 again and pull the blade 30 farther up into the sheath, the user is unable to do this. As a safety precaution, due to the length of the slot 59, the first pin 24 hits the end wall 57 of the slot 59, and therefore the blade 30 and blade handle 40 can't be drawn further into the sheath risking damage to the blade by possibly hitting the inner wall of the sheath 10 as it would be drawn further in.

The instrument is inserted into the body while the blade is fully withdrawn to prevent unnecessary cutting with the blade edge. Once at the operative site, the surgeon can expose the blade either partially or fully (whichever is desired), by deflecting the cantilever spring 22 and sliding the sheath back toward the proximal end until the pin 26 is appropriately locked into position for either the partially or fully exposed blade position. The surgeon can hold the instrument and effect blade position changing all with one hand due to the convenient design of the engaging means.

Another safety feature of this invention prevents the blade 30 and blade handle 40 from sliding out of the sheath further than the fully exposed blade position. This prevents the blade from accidentally sliding out too far and potentially making an unintentional and unsafe cut with the blade. This is prevented due to the larger diameter of the handle extension 32 which is assembled after the blade handle 40 is inserted through the sheath 10 and protrudes from the proximal end of the sheath 10. Looking at FIG. 7, the pin is in the most proximal hole and the blade is fully exposed. If the spring 22 is deflected, disengaging pin 26 from the most proximal hole 58, and the user attempts to further expose the blade 30 and blade handle 40, the handle 40 moves only a fraction forward which is enough to move pin 26 out of direct alignment with the hole 58. Then with the spring 22 deflected and the pin 26 resting on top of the outer diameter of the handle 40, the larger outer diameter of the handle extension 32 interferes with the inner diameter of the sheath 10 preventing the handle extension 32 from entering the proximal end of the sheath 10, hence preventing further forward movement of the blade handle 40 through the sheath 10 which safely limits how far the blade 30 is capable of protruding.

Therefore, to remove the handle 40 from the sheath or to change blades 30, the handle extension 32 is simply removed from the handle 40, and the handle 40 can then be withdrawn as shown in FIG. 8. As can be easily seen, this instrument enables the blades 30 to be replaced during surgery if necessary without having to advance the new blade 30 through the sheath 10 risking dulling of the blade, and without having to completely remove the handle 40 from the sheath 10.

While this combination sheath and retractable surgical instrument has been described in terms of a particularly advantageous embodiment, that of a sheath with an associated scalpel blade for use in arthroscopy, it is understood that the present invention could be adapted for use with other manual arthroscopy or endoscopy instruments, such as forceps, scissors, punches, and probes. The sheath could be used to provide atraumatic introduction of these instruments into closed surgical sites. It is understood that adaptions would have to be made to accommodate the various working ends of these tools. Also, the sheath/instrument combination could be used for other surgical procedures besides arthroscopy or endoscopy. For example, the sheath could be used in association with various biopsy tools to facilitate introduction of the biopsy tool across outlying tissue layers to the structure or organ to be sampled.

While this invention has been described and exemplified in terms of a particularly advantageous embodiment, those skilled in the art can appreciate that modification can be made without departing from the spirit and scope of this invention.

I claim:

1. A surgical tool comprising:
   (a) an elongated handle having a distal end portion and an elongated main body portion, said distal end providing a working end of the surgical tool;
   (b) a protective tubular outer sheath for surrounding said elongated handle, said sheath having a distal end, a proximal end and an intermediate portion therebetween, said handle being insertable into the sheath from the distal tubular opening of the sheath, and wherein said sheath includes a stepped portion wherein said proximal end portion of the sheath has a larger diameter than the distal and intermediate portions; and
   (c) an engaging means operative between the sheath and the handle, said engaging means providing a plurality of functional positions for the handle to be selectively positioned within the sheath, and wherein said engaging means interacts internally between the sheath and the handle components and includes a protrusion means on one component and an indentation means on the other component, which cooperatively engage with each other, and wherein said sheath includes a resilient cantilever spring mechanism enabling said engaging means to disengage upon application of pressure thereto and wherein said sheath further includes first and second proximal tubular portions, said first and second portions being interconnected by the cantilever spring mechanism, said spring mechanism being a thin interconnecting resilient strip, said first portion further integrally connected to the intermediate portion of the sheath and said second portion being the most proximal portion of the sheath, said disengaging occuring upon application of pressure to one of said portions.

2. A surgical tool as described in claim 1 wherein said disengaging occurs upon application of pressure to said second portion.

3. A surgical tool as described in claim 1 wherein said tool further includes a means for preventing rotation of the handle means with respect to the sheath, and for positively orienting the direction of the blade with respect to said sheath.

4. A surgical tool as described in claim 3 wherein said means for preventing rotation between the handle and sheath components includes a slot in one component and a protruding alignment pin on the other component which cooperate for allowing said alignment pin to longitudinally slide in said slot while preventing rotation between the sheath and the handle.

5. A surgical tool as described in claim 4 wherein said slot and alignment pin cooperates for preventing the handle from being withdrawn out of the sheath through the proximal portion of the sheath.

6. A surgical tool as described in claim 1 wherein The tool is a cutting instrument and said handle includes replaceable blades secured thereto, said blades being replaceable without having to completely remove the handle portion from the sheath.

7. A surgical tool as claimed in claim 1 wherein said handle further comprises a separable handle extension attachable to the proximal end of said handle.

8. A surgical tool as claimed in claim 7 wherein said handle extension is sized in diameter so as to prevent the handle extension from entering the proximal end of the sheath, and to prevent the blade from accidentally extending further than the fully exposed blade position.

9. A surgical tool comprising:
   (a) an elongated handle having a distal end portion and an elongated main body portion, said distal end providing a working end of the surgical tool;
   (b) a protective tubular outer sheath for surrounding said elongated handle, said sheath having a distal end, a proximal end and an intermediate portion therebetween, said handle being insertable into the sheath from the distal tubular opening of the sheath, and wherein said sheath includes a stepped portion wherein said proximal end portion of the sheath has a larger diameter than the distal and intermediate portions; and
   (c) an engaging means operative between the sheath and the handle, said engaging means providing a plurality of functional positions for the handle to be selectively positioned within the sheath, and wherein said engaging means interacts internally between the sheath and the handle components and includes a protrusion means on one component and an indentation means on the other component, which cooperatively engage with each other, and wherein said sheath includes a resilient cantilever spring mechansism enabling said engaging means to disengage upon application of pressure thereto, and wherein said sheath further includes first and second proximal tubular portions, said first and second portions being interconnected by the cantilever spring mechanism, said spring mechanism being a thin interconnecting resilient strip, said first portion further integrally connected to the intermediate portion of the sheath and said second portion being the most proximal portion of the sheath, said disengaging occuring upon application of pressure to said second portion, and wherein the protrusion means includes a protruding engagement pin extending from the inside diameter of the second proximal tubular portion of the sheath and the indentation means includes a plurality of depressed holes in the handle means which can each be selectively engaged with the protruding engagment pin, each hole corresponding to a different functional position for positioning the handle relative to the sheath.

10. A surgical tool as described in cliam 9 further adapted to be holdable and maneuverable with one hand wherein the protruding engagement pin protrudes from the inner wall of the second proximal portion of the sheath such that the application of pressure by the hand to the portion of the second proximal portion of the sheath opposite the engagement pin will deflect the cantilever spring and raise the pin out of engagement from the hole in the handle enabling the handle to be moved relative to the sheath to the desired position.

11. A surgical tool as described in claim 10 wherein the protruding engagement pin protrudes from the portion of the inner wall of the second proximal portion of the sheath adjacent the thin strip.

12. A surgical tool as described in claim 10 wherein the protruding engagement pin protrudes from the portion of the inner wall of the second proximal portion of the sheath opposite the thin strip.

13. A surgical tool as claimed in claim 9 wherein said tool includes at least two functional positions, a first position in which the working end of the surgical tool is completely withdrawn into the sheath and a second position in which the working end of the tool is exposed enabling the working end to function for its intended purpose.

14. A surgical tool as described in claim 9 wherein said tool includes at least three functional positions, a first position in which the working end of the surgical tool is completely withdrawn into the sheath and a second position in which the working end is partially exposed enabling the working end to function for its intended purpose in tight quarters, and a third position in which the working end is fully exposed enabling the working end to function for its intended purpose where space is not constrained.

* * * * *